US008673547B2

(12) United States Patent  
Gage

(10) Patent No.: US 8,673,547 B2
(45) Date of Patent: Mar. 18, 2014

(54) METHOD FOR ISOLATION OF AFTERBIRTH DERIVED CELLS

(75) Inventor: Frederick A. Gage, Kensington, MD (US)

(73) Assignee: Hemacell Perfusion, Inc., Silver Spring, MD (US)

( * ) Notice: Subject to any disclaimer, the term of this patent is extended or adjusted under 35 U.S.C. 154(b) by 534 days.

(21) Appl. No.: 12/530,236

(22) PCT Filed: Mar. 7, 2008

(86) PCT No.: PCT/US2008/056201
§ 371 (c)(1),
(2), (4) Date: Sep. 8, 2009

(87) PCT Pub. No.: WO2008/109816
PCT Pub. Date: Sep. 12, 2008

(65) Prior Publication Data
US 2010/0041009 A1 Feb. 18, 2010

Related U.S. Application Data

(60) Provisional application No. 60/893,710, filed on Mar. 8, 2007.

(51) Int. Cl.
*A01N 1/00* (2006.01)
*A01N 1/02* (2006.01)
*C12M 1/00* (2006.01)

(52) U.S. Cl.
USPC .......................................... 435/1.2; 435/283.1

(58) Field of Classification Search
USPC ................................. 435/1.2, 283.1
See application file for complete search history.

(56) References Cited

U.S. PATENT DOCUMENTS

| | | | |
|---|---|---|---|
| 3,632,473 A | 1/1972 | Belzer et al. | |
| 3,862,002 A | 1/1975 | Sanders | |
| 4,065,264 A | 12/1977 | Lewin | |
| 5,752,929 A | 5/1998 | Klatz et al. | |
| 6,461,645 B1 | 10/2002 | Boyse et al. | |
| 6,811,965 B2 | 11/2004 | Vodovotz et al. | |
| 6,953,655 B1 | 10/2005 | Hassanein | |
| 6,977,140 B1 | 12/2005 | Owen et al. | |
| 7,011,623 B2 | 3/2006 | Clerin et al. | |
| 7,014,990 B2 | 3/2006 | Polyak et al. | |
| 7,045,148 B2 | 5/2006 | Hariri et al. | |
| 7,060,494 B2 | 6/2006 | Bhat | |
| 7,255,879 B2 | 8/2007 | Hariri | |
| 7,311,904 B2 | 12/2007 | Hariri | |
| 7,468,276 B2 | 12/2008 | Hariri | |
| 8,057,788 B2 | 11/2011 | Hariri | |
| 8,329,468 B2 | 12/2012 | Takebe | |
| 2002/0123141 A1* | 9/2002 | Hariri | 435/366 |
| 2003/0032179 A1 | 2/2003 | Hariri | |
| 2003/0180269 A1 | 9/2003 | Hariri | |
| 2004/0219136 A1 | 11/2004 | Hariri | |
| 2005/0032209 A1 | 2/2005 | Messina et al. | |
| 2005/0037491 A1 | 2/2005 | Mistry et al. | |
| 2005/0272148 A1 | 12/2005 | Hariri | |
| 2006/0153816 A1 | 7/2006 | Brown et al. | |
| 2006/0153818 A1 | 7/2006 | Dhanaraj et al. | |
| 2006/0154367 A1 | 7/2006 | Kihm et al. | |
| 2006/0182724 A1 | 8/2006 | Riordan | |
| 2007/0190649 A1 | 8/2007 | Gage | |
| 2008/0131410 A1 | 6/2008 | Hariri | |
| 2009/0123437 A1 | 5/2009 | Takebe | |

FOREIGN PATENT DOCUMENTS

| | | | |
|---|---|---|---|
| CN | 1548529 | 11/2004 | |
| WO | WO02064755 | 8/2002 | |
| WO | WO03068937 | 8/2003 | |
| WO | 2005001081 A1 | 1/2005 | |
| WO | WO 2005/001081 * | 1/2005 | ............... C12N 5/08 |
| WO | WO 2005/056747 * | 6/2005 | |
| WO | WO2007047468 | 4/2007 | |
| WO | WO2007078183 | 7/2007 | |

OTHER PUBLICATIONS

Assad et al. "Placental compliance during fetal extracorporeal circulation" J Appl Physiol 90: 1882-1886, 2001.*
Leitch et al. "Vasodilator Actions of Urocortin and Related Peptides in the Human Perfused Placenta in Vitro" Journal of Clinical Endocrinology and Metabolism vol. 83, No. 12 pp. 4510-4513, 1998.*
Ludwig et al. "Derivation of human embryonic stem cells in defined conditions" Nature Biotechnology vol. 24 No. 2 Feb. 2006 with Supplementary Figure 1, 4pgs.*
Techniques and Instrumentation in Analytical Chemistry "Flow Injection Analysis—A Practical Guide Chapter 3 Components of FIA" vol. 10, 1989, pp. 29-65.*
Technical Resource Library from Cole-Parmer "Reducing Pulsation in Peristaltic Pumping Systems" 4 pages posted Aug. 25, 2006 at http://www.coleparmer.com/TechLibraryArticle/579.*
Langeron et al. "Voluven®, a Lower Substituted Novel Hydroxyethyl Starch (HES 130/0.4), Causes Fewer Effects on Coagulation in Major Orthopedic Surgery than HES 200/0.5" Anesth Analg 2001;92:855-62.*
Bornstein et al. "A Modified Cord Blood Collection Method Achieves Sufficient Cell Levels for Transplantation in Most Adult Patients" Stem Cells 2005;23:324-334, available online in Mar. 1, 2005.*

(Continued)

*Primary Examiner* — Thane Underdahl
(74) *Attorney, Agent, or Firm* — Mendelsohn, Drucker & Dunleavy, P.C.

(57) ABSTRACT

A method for extracting cells from afterbirth tissue, including placing the afterbirth into a perfusion circuit prior to exsanguination, extracting the cells from the afterbirth with digestive enzymes and mechanically recovering cells from the digested afterbirth tissue, and isolating the cells from the perfusate and digestion mix. Also disclosed is a cell line derived from afterbirth using the two-step pulsatile perfusion extraction method.

19 Claims, 8 Drawing Sheets

(56) References Cited

OTHER PUBLICATIONS

Baicu et al. "The role of preservation solution on acid-base regulation during machine perfusion of kidneys" Jan.-Feb. 2006;20(1):113-21, available online Oct. 31, 2005.*
Moore et al. "A simple perfusion technique for isolation of maternal intervillous blood mononuclear cells from human placentae" Journal of Immunological Methods 209 (1997) 93-104.*
Ameida Proada—Formation of Human—Blood—2004—104—p. 2582-2590.
Azisa—Engraftment and migration—Proc Natl Acad 1998 p. 3908-3913.
Barker—Searching for unrelated donor—Biol Blood Marrow Tr. 2002—p. 257-260.
Bertolini—Comparative study of differnt—J Hematother—Feb. 1995—4—p. 29-36.
Bessems—Improved Rat Liver Preservation—Liver Transplantation, v 11—5—May 2005—p. 539-546.
Bhattacharya—Direct Identification—Invest Ophthalmol Vis Sci v 44 Jun. 2003 p. 2764-2773.
Bicknese—Human umbilical cord blood—Cell Transplant 11—2002—p. 261-264.
Brazelton—From marrow to brain—Science 190—2000 p. 1775-1779.
Cai—In search of stemness—Inter Soc for Exp Hematology—Elsevier 32—2004 p. 585-598.
Cai—Membrane properties of rat—J Neurochem 2004—88—p. 212-226.
Cai—Properties of a fetal multipotent—Dev Biol 251—2002 p. 221-240.
Camargo—Hematopoietic myelomonocytic—J Clin Invest 113—2004—p. 1266-1271.
Chen—Human Umbilical Cord Blood—Stem Cells—Ohio—2005 p. 1560-1571.
Cogle—Bone marrow transdifferentiation—Lancet 363—2004—p. 1432-1437.
Conneally—Expansion in Vitro of transplantable—Proceedings of Nat Aca Sci USA—v 94-18-1997—p. 9836-9841.
Corti—Transplanted ALDH—Hum Mol Genet 15—2006—p. 167-187.
Donaldson—Impact of obstetric factors—Br J of Haematology 106—1999—p. 128-129.
Eglitis—Hematopoietic cells—Proc Natl Acad Sci USA 94—1997—p. 1080-1085.
Escolar—Transplantation of umbilical-cord—N Engl J Med 352—2005—p. 2069-2087.
Ferrari—Muscle regeneration by bone marrow-derived—Science 279—1998—p. 1528-1530.
Forraz—Characterization of a lineage-negative—Stem cells 22—2004—p. 100-108.
Fortunel—Comment on Stemness—Science 302—5 pages.
Gage—A Comparison study of the Belzer—Transplant Proc 29—1997—p. 3643.
Gekas—The Placenta is a niche for hematopoietic—Dev Cell 8—2005—p. 365-375.
George—Factors associated with parameters of engraftment—Transplantation and Cellular Engineering—v 46—Oct. 2006—13 pages.
Gluckman—Outcome of cord-blood transplantation—Eurocord Transplant Grp—337—6—p. 373-381.
Goodwin—Multilineage differentiation activity—Biol Blood Marrow Transplant 7—2001—3 pages.
Harris—Collection separation and cryopreservation—Bone Marrow transplantation 13—1994—p. 135-143.
Hruban—Fluorescence in situ—Am J Pathol 142—1993—p. 975-980.
Jaatinen—Global Gene Expression Profile—Stem Cells 24—2006—p. 631-641.
Kim—The multidrug resistance transporter—Clin Cancer Res 8—2002—p. 22-28.
Korbling—Hepatocytes and epithelial—N Engl J Med 346—2002—p. 738-746.
Kuci—Identification of a novel class—Blood 101—2003—p. 869-876.
Kucia—Morphological and molecular—Leukemia 21—2007—p. 297-300.
Kurtzberg—Placental Blood as a Source—N Eng J Med 335—1996—p. 157-166 + Correction 1997—3 pages.
Lagassi—Purified hematopoietic stem cells—Nat Med 6—2000—p. 1229-1234.
Lasky—In ugtero or ex utero cord—Transfusion 42—2002—3 pages.
Laughlin—Ourcomes after transplantation—N Engl J Med 351—2004—p. 2265-2275.
McGuckin—Production of stem cells—Cell Prolif 38—2005—4 pages.
McGuckin—Umbilical cord blood stem—Exp Cell Res 295—2004—p. 350-359.
Mezey—Turning blood into brain—Science 290—2000—p. 1779-1782.
Migishima—Full reconstitution of hematopoietic—Transplantation 75—2003—p. 1820-1826.
Muller—Cardiomyocytes of noncardiac—Circulation 106—2002—p. 31-35.
Okamoto—Damaged epithelia regenerated—Nat Med 8—2002—p. 1011-1017.
Ottersbach—The murine placenta contians hematopoietic—Dev Cell 8—2005—p. 377-387.
Parmar—Sca+CD34—murine side—Exp Hematol 31—2003—p. 244-250.
Parolini—Concise Review Isolation—Stem Cells 26—2008—p. 300-311.
Petersen—Bone marrow as a potential—Science 284—1999—p. 1168-1170.
Quaini—Chimerism of the traqnsplanted heart—N. Engl J. Med 346—2002—p. 5-15.
Rubinstein—Outcomes among 562 recipients—N. Engl J Med 339—1998—p. 1565-1577.
Addison, et al., "Metabolism of Prednisolone by the Isolated Perfused Human Placental Lobule", J. Steroid Biochem. Molec. Biol. vol. 39, No. 1, pp. 83-90, 1991.
Matsuoka, et al., "Pulsatile Perfusion Reduces the Incidence of Delayed Graft Function in Expandd Criteria Donor Kidney Transplantation", American Journal of Transplantation, 2006, 6, pp. 1473-1478.
Hammon, John W., "Extracorporeal Circulation: Perfusion System", Cardiac Surgery in the Adult. New York: McGraw-Hill, 2008, pp. 350-370 Chapter 12A.
Murkin, et al., "Cardiopulmonary Bypass, Myocardial Management and Support Techniques: A Randomized Study of the Influence of Perfusion Technique and pH Management Strategy in 316 Patients Undergoing Coronary Artery Bypass Surgery: II. Neurologic and Cognitive Outcomes", J. Thorac Cardiocasc Surg 1995, 110, pp. 349-362.
Thompson, et al., "The Influence of Pulsatile and Nonpulsatile Extracorporeal Circulation on Fluid Retention Following Coronary Artery Bypass Grafting", Perfusion 1992, 7, pp. 201-211.
Belvedere, et al., "Increased Blood Volume and CD34+CD38—Progenitor Cell Recovery Using a Novel Unbilical Cord Blood Collection System", Stem Cells, 2000, 18, pp. 245-251.
Moore, et al., "A Simple Perfusion Technique for Isolation of Maternal Intervillous Blood Mononuclear Cells from Human Placentae", Journal of Immunological Methods, 1997, vol. 209, pp. 93-104.
Dougherty, et al., "Characterization of Perfusion Pump Performance Using Harmonic Analysis", Bioengineering Conference, ASME, 2001, 50, pp. 501-502.
Davis, et al., "Maximal Cord Blood Recovery and CD34+ Progenitor Cell Collection Using Machine Pulsatile Perfusion of Placentas", Blood (ASH Annual Meeting Abstracts) 2006, 108: Abstract 3643, American Society of Hematology, 5 pgs.
Rubinstein—Storec placental blood—Blood 81—1993—p. 1679-1690.

(56) References Cited

OTHER PUBLICATIONS

Sanchez-Ramos—Adult bone marrow stromal—Exp Neurol 164—p. 247-256.
Sanchez-Ramos—Expression of neutral markers—Exp Neurol 171—2001—p. 109-115.
Sanchez-Ramos—Natural cells derived from adult bone—Exp Neurol 69—2002—p. 880-883.
Scharenberg—the ABCG2 transporter—Blood 99—2002—p. 507-512.
Shlebak—the impact of antenatal and perinatal—Br J Haematol 103—1998—3 pages.
Storms—Isolation of primitive human—Proc Natl Acad Sci USA 96—1999—p. 9118-9123.
Takebe—Preliminary Findings on the use of Pulsatile—Transfusion—v 49—Sep. 9, 2009—p. 1911-1916.
Takebe—Generation of dual resistance—Mol Ther 3—2001—p. 88-96.
Takebe—Methotrexate selection—Cancer Gene Ther 9—2001 p. 308-320.
Theise—Liver from bone marrow in humans—Hepatology 32—2000—p. 11-16.
Turner—A modified harvest technique—Bone marrow transplantation—1992—2 pages.
Wagner—Successful transplantation of HLA—Blood 88—1996—p. 795-802.
Wagner—Transplantation of unrelated donor—Blood 100—2002—p. 1611-1618.
Wagner—Umbilical cord and placental blood—J. Hematother 1—1992—p. 167-173.
Wang—Albumin-expressing hepatocyte-like—Blood 101—2003—p. 4201-4208.
Wang—Cell fusion is the principal source—Nature 422—2003—p. 897-901.
Zhou—The ABC transporter Bcrp—Nat Med 7—2001—p. 1028-1034.
Zigava—Human umbilical cord blood—Cell Transplant 11—2002—p. 265-274.
Complete file history of U.S. Appl. No. 11/654,553, 225 pqs.

* cited by examiner

METHOD FOR ISOLATION OF AFTERBIRTH DERIVED CELLS

BACKGROUND OF THE INVENTION

1. Field of the Invention

The present invention relates to methods for isolating cells from afterbirth tissue employing pulsatile perfusion.

2. Brief Description of the State of the Art

The afterbirth tissue, an ephemeral organ and associated tissues that develop naturally as a result of gestation, is a source of cellular matter that can be used in biological research and for therapeutic procedures. Stem cells derived from afterbirth tissue are increasingly considered desirable due to the fact that certain cells are pluripotent and believed to have a high potential for research and therapeutic applications.

Umbilical cord blood (UCB) has been identified as an important source of stem cells. Most of the stem cells recovered from UCB are thought to be useful in making blood and blood products and are called "hematopoietic" stem cells (HSC). Currently, collection of UCB is difficult and does not always provide enough useable stem cells. Researchers can use UCB-derived stem cells for transplantation into people who have lost their red and white blood cells through disease (like leukemia or lymphoma) or radiation (which is a common side-effect of chemotherapy or from nuclear radiation from atomic bombs or nuclear power accidents). Recent studies have demonstrated that using greater numbers of UCB-derived HSC increases the success of these kinds of transplants; however, approaches to growing more transplantable HSC from UCB in cell culture have been widely unsuccessful.

Methods for "perfusion" of organs for transplant have been used for the past 15 to 20 years. Perfusion science seeks to maintain an organ's natural function using mechanical means. Perfusion has been mostly utilized in cardiac-thoracic surgery, vascular surgery, and for preservation of organs for transplantation. See, for example, U.S. Pat. No. 6,811,965.

The aim of this invention is to increase numbers of stem cells and other primary cells recovered from the afterbirth tissue in comparison to collection from UCB or independent perfusion of the exsanguinated placenta. Ideally, this should result in more successful transplants and treatments and more cellular matter for use in biological research. The simplicity, speed of collection and the total number of useable cells collected could clinically widen the applicability of stem cell transplants in adults.

There is also a substantial and growing body of evidence that stem cells derived from afterbirth tissue may have broader potential for becoming non-hematopoietic (not blood related) cells, such as liver cells, heart cells and nerve cells. If proven true, non-HSC recovered from the perfusion of afterbirth tissue could prove to be a powerful tool in stem cell research.

There are at least two methods typically used to obtain stem cells from the umbilical cord or placenta. The first method involves simply draining blood from the placenta and/or umbilical cord into a closed sterile collection bag using gravity. U.S. Pat. No. 7,045,148 describes a method which uses perfusion to extract cells from the placenta after exsanguinations of the umbilical cord and placenta.

At least one researcher has flushed the placenta with perfusate through the arterial-vein circuit to eliminate tissue residual blood; however, there do not appear to have been any reported extractions of cord blood components, in tandem with the placenta, using pulsatile perfusion or perfusion involving digestive enzymes.

An objective of this invention is to provide an improved method for obtaining pluripotent stem cells, as well as viable primary cells that cannot be described as stem cells because they are incapable of self-renewal.

SUMMARY OF THE INVENTION

In one aspect, the present invention employs pulsatile perfusion to extract cells from afterbirth tissue. In this aspect, the method involves the steps of:
  a) placing the afterbirth tissue into a perfusion circuit,
  b) extracting cells from said afterbirth tissue by pulsatile perfusion to produce a perfusate containing cells, and
  c) isolating cells from the perfusate.

Another aspect of this invention involves the same process as described above, with the additional step of adding enzymes to the perfusion process.

An advantage of certain embodiments of the invention is that the extraction may produce more than twice as many viable cells from the intact afterbirth tissue than can achieved by collection from UCB or the placenta independently.

DETAILED DESCRIPTION OF THE PREFERRED EMBODIMENTS

Figure 1:
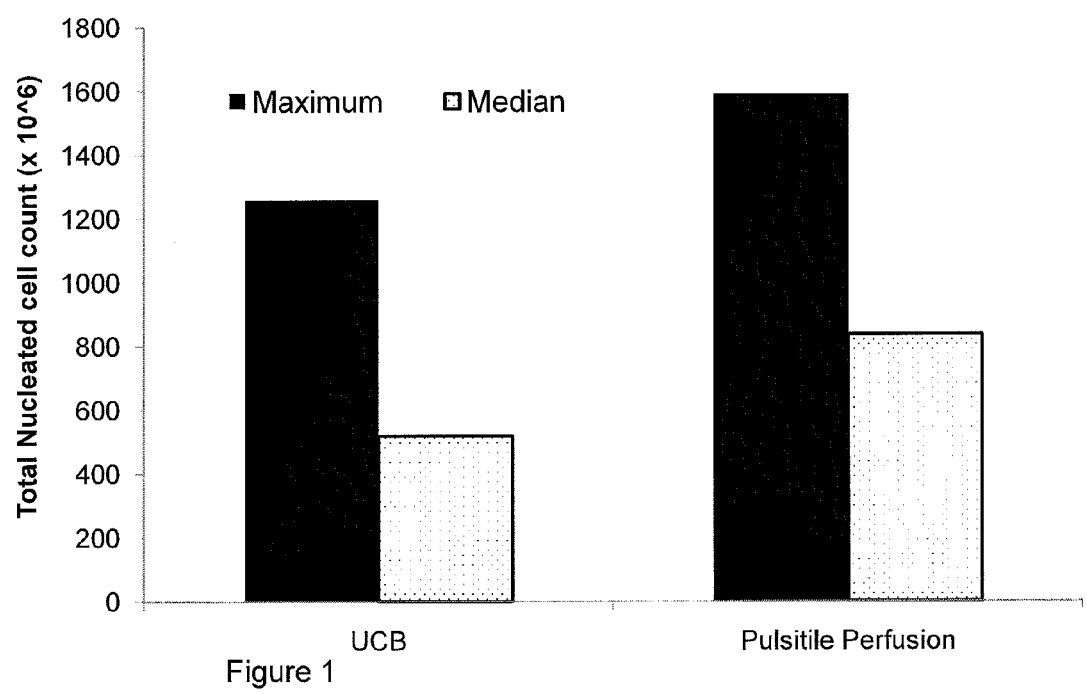
FIG. 1 is a graph, which plots the maximum Total Nucleated Cell (TNC) count recovered from cord blood samples extracted by syringe in comparison to afterbirth tissue perfusion according to the method of the present invention (n=11 isolations).
Figure 2:
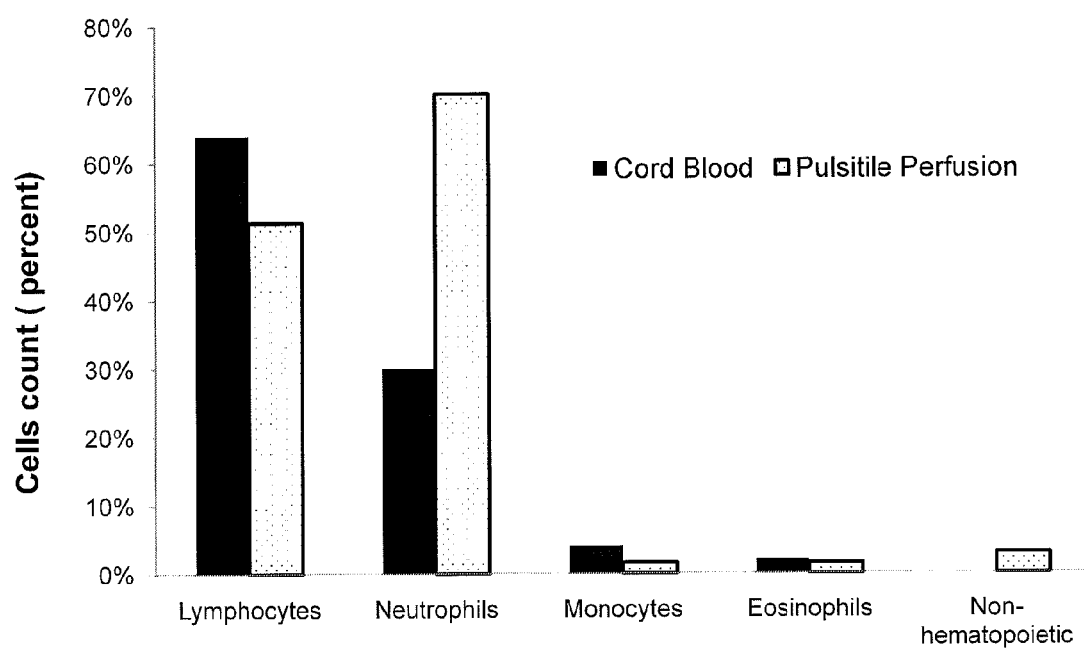
FIG. 2 is a graph, which plots the percentage of recoverable white blood cells by type of cell contained in a cord blood sample extracted by syringe in comparison to afterbirth tissue perfusion according to the method of the present invention.
Figure 3:
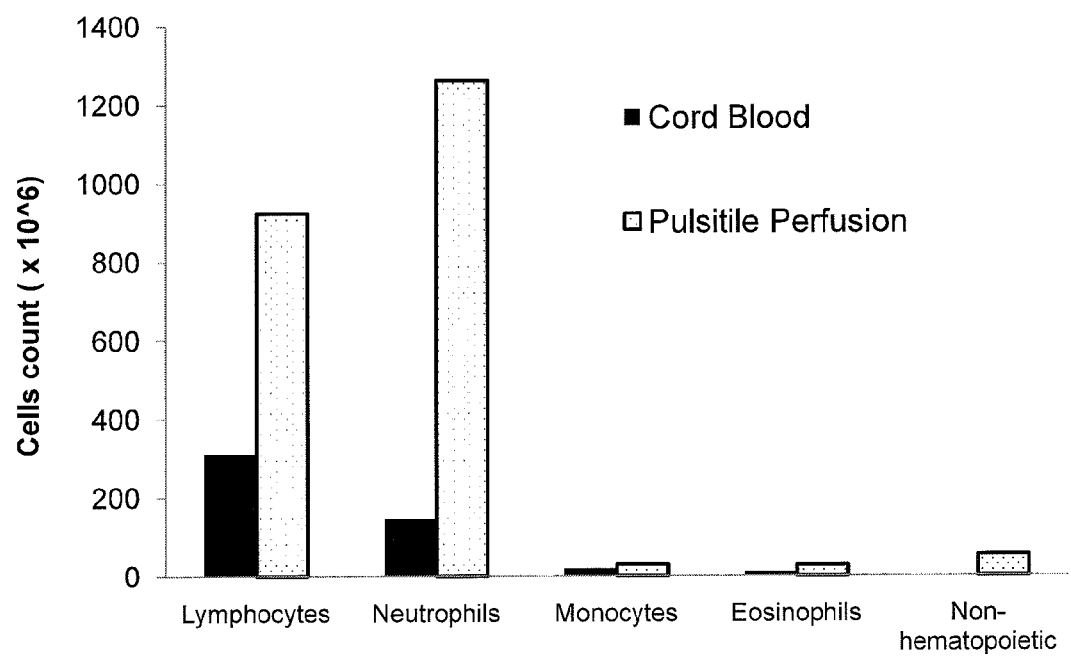
FIG. 3 is a graph, which plots the absolute number of cells vs. cell yield by type of cell contained in a cord blood sample extracted by syringe prior in comparison to perfusion of the afterbirth tissue according to the method of the present invention.
Figure 4A:
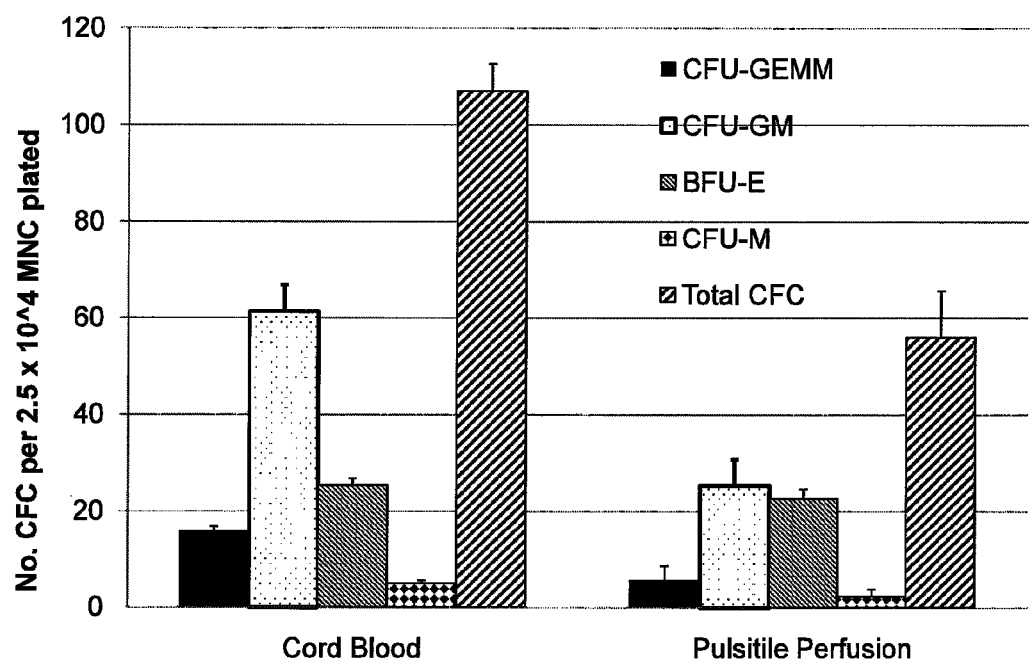
FIG. 4A is a graph which plots the cloning efficiency achieved from a mononuclear cell preparation derived from a syringe cord blood sample and an independent afterbirth tissue perfusate.
Figure 4B:
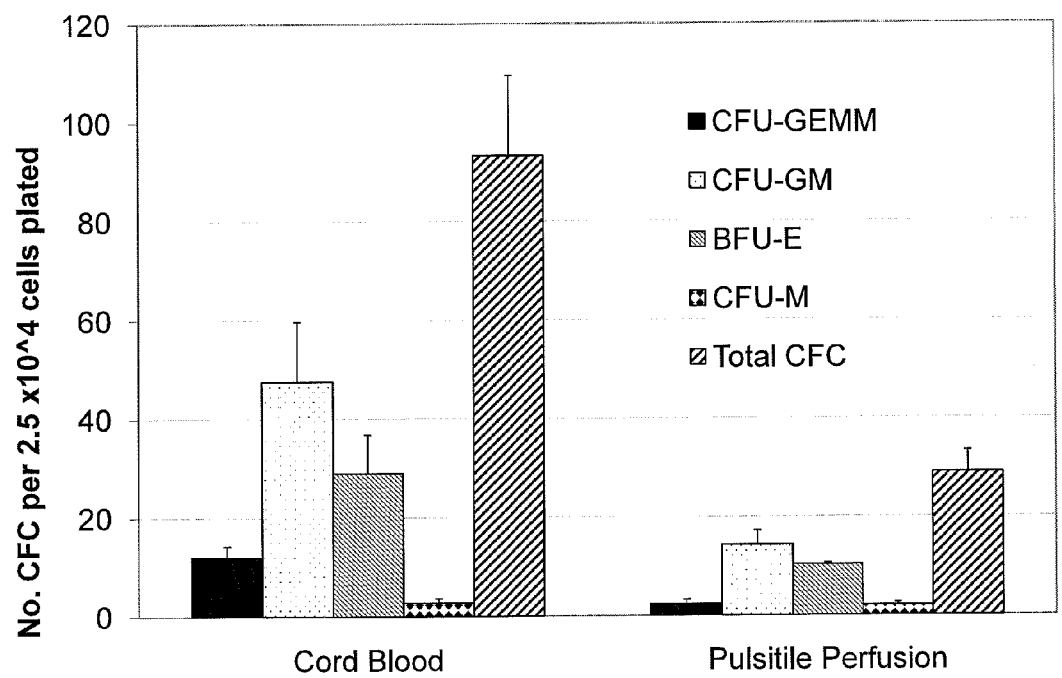
FIG. 4B is a graph which plots the cloning efficiency achieved from a lysed cell preparation derived from a syringe cord blood sample and an independent afterbirth tissue perfusate sample.
Figure 4C:
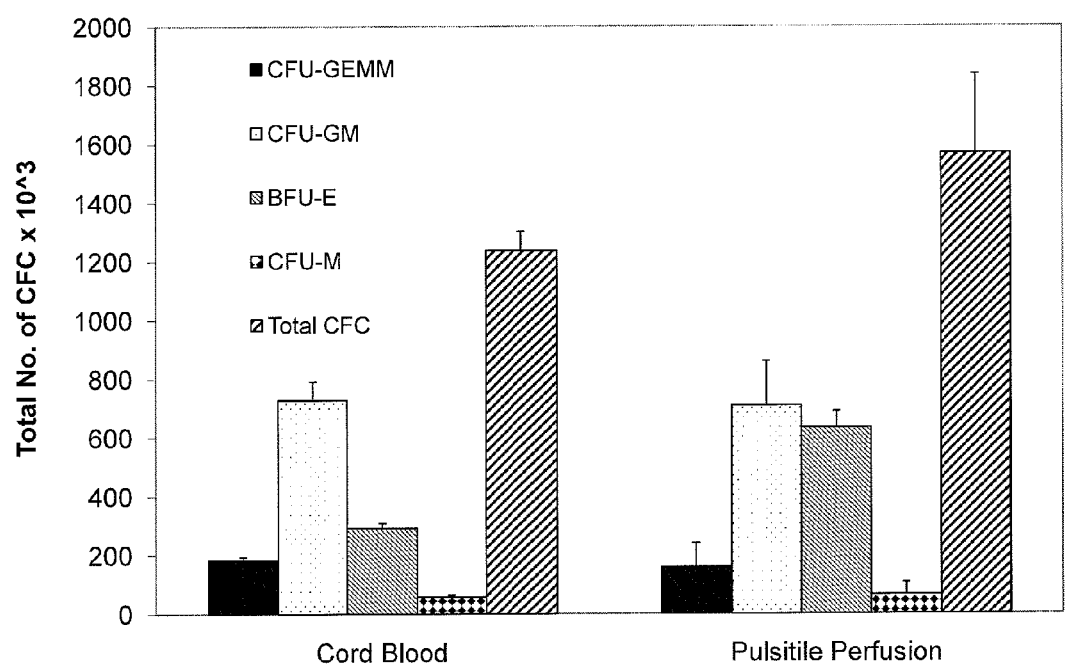
FIG. 4C is a graph of total amount of progenitor cells present in a syringe cord blood sample and the independent afterbirth tissue perfusate with respect to mononuclear cells.
Figure 4D:
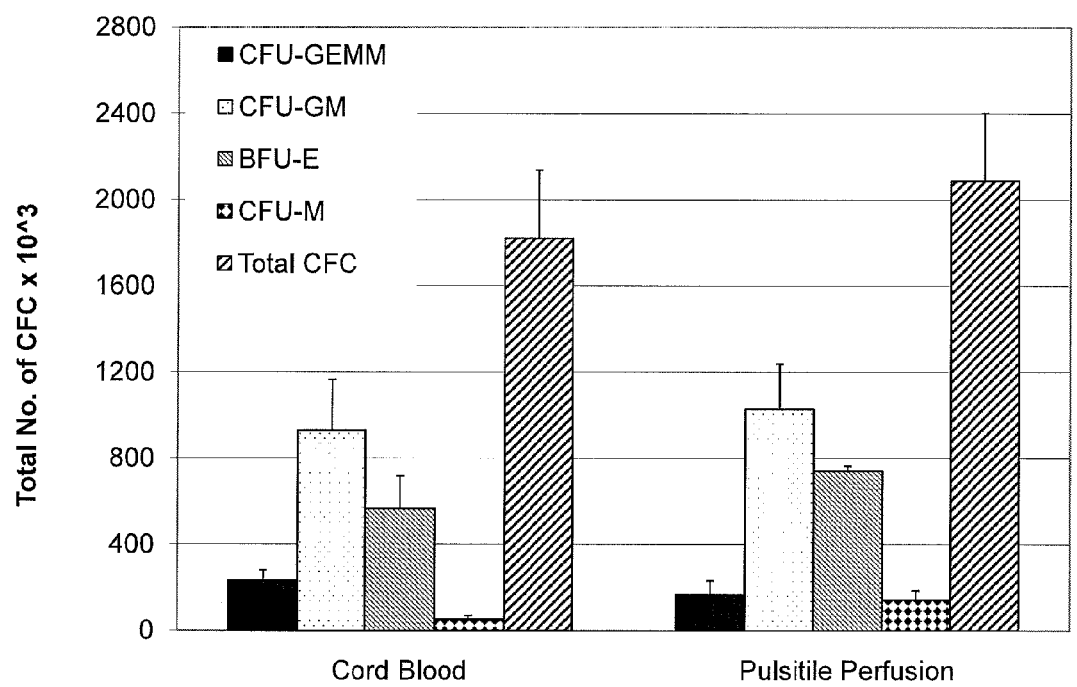
FIG. 4D is a graph of total amount of progenitor cells present in the syringe cord blood sample and the independent afterbirth tissue perfusate with respect to lysed white blood cells.
Figure 5:
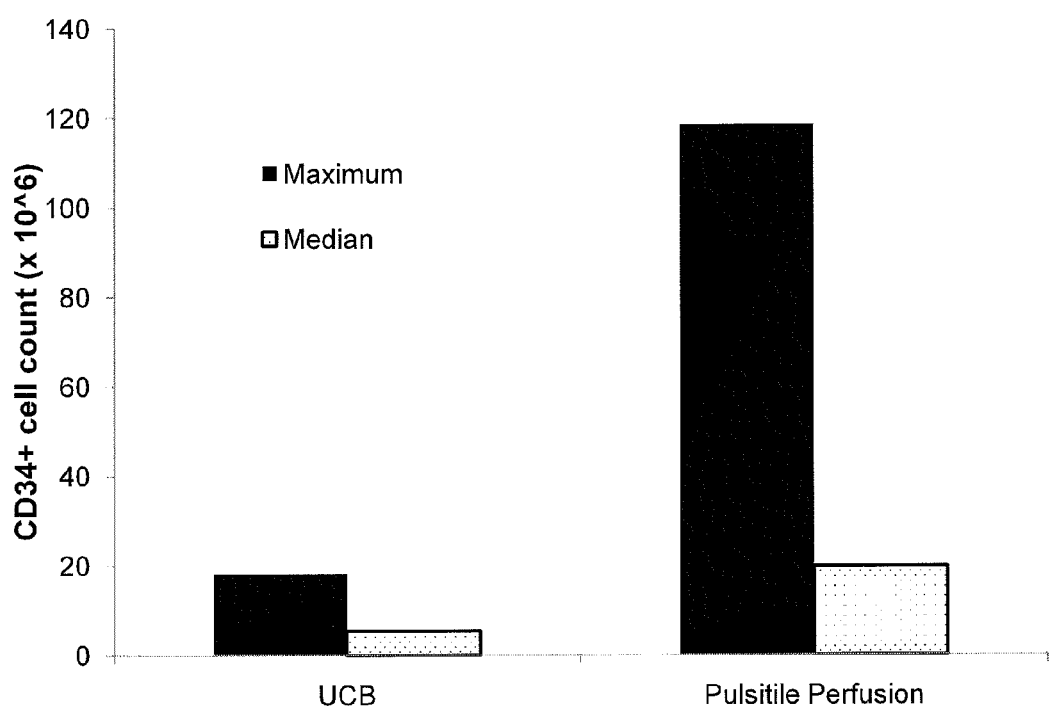
FIG. 5 is a graph of the maximum number of CD34+ cell yield and also by attribution to the cord blood sample and cells extracted by afterbirth tissue perfusion according to the method of the present invention (n=11 isolations).

For the purpose of the present invention, afterbirth tissue is obtained from mammalian sources, including human. Afterbirth tissue includes the placenta with attached umbilical cord following either a vaginal or cesarean delivery. The recoverable cells include any cell type present in afterbirth tissue and membranes, including cells originating from the three major germ layers, endoderm, ectoderm or mesoderm, as well as primary cells from the circulatory system and other cell types derived from tissues contributed by the mother.

The source of viable cells is an umbilical cord attached to the placenta (herein collectively referred to as "afterbirth tissue"). The umbilical cord may be clamped or tied off after the child is delivered. Preferably, an effective amount of an anticoagulant such as heparin will be administered to the placental arteries and/or umbilical vein. In an illustrative example a bolus of 10,000 units of heparin is administered, for example, as 5,000 units into each artery or vein. The afterbirth tissue may then be placed into multiple sterile isolation bags, with each isolation bag preferably being individually tied shut. The packaged afterbirth tissue is preferably cooled to approximately 0° C. prior to perfusion to preserve the organ and associated tissues. For example, the afterbirth tissue may be placed into an insulated container with wet ice to await delivery to a perfusion laboratory.

An advantage of perfusing afterbirth tissue for recovery of pluripotent cell types such as stromal cells is that a far greater number of cells can be recovered from the afterbirth tissue than from an embryo. More particularly, only about 30 to 50 stem cells can be obtained per embryo. In comparison, about $2 \times 10^9$ stem cells can be extracted from afterbirth tissue using perfusion.

We have shown that "perfusion" of afterbirth tissue can produce at least twice and, more preferably, three and one half times as many HSC cells when compared to traditional UCB collection procedures. Furthermore, perfusion results in the isolation of many of different types of cells that can be isolated, collected and used in many other applications.

The method of the present invention may employ any conventional pulsatile perfusion device. The construction and operation of such pulsatile perfusion devices is well known to those of ordinary skill in the art. See, for example, U.S. Pat. Nos. 3,632,473, 4,065,264, and 5,752,929, the disclosures of which are hereby incorporated by reference herein. Such machines typically include a perfusion circuit having a storage compartment and a pulsatile perfusion pump adapted to pump a perfusion solution through an organ. The pulsatile perfusion pump may be a centrifugal perfusion pump, a roller perfusion pump, or a mechanical pulsatile perfusion pump, for example.

In the present invention, the perfusion machine is adapted to pump a perfusion solution through the afterbirth tissue into a storage compartment to collect the perfusion solution, which will contain materials extracted from the afterbirth tissue, such as stem cells and other primary cells originating form the afterbirth tissue.

One example of a pulsatile rate and mode would be that which simulates the pulsed flow of a beating heart. The rate and combination of pulses from the pulsatile perfusion pump could be determined by the operator. For example, the pump could deliver a preset fluid volume, fluid at a preset pressure, or fluid at a preset flow rate, in a series of one or more pulses. Once this fluid volume was delivered, the pump could be brought into reverse, either automatically or manually. This reversal would involve a series of one or more pulses to extract a volume approximately equivalent to that which was delivered, or other predetermined volume, back into the reservoir of the device. This cycle could continue for as long as desired. Alternately, the pump could be set to pulse only in a forward direction and/or operate in a non-cyclic manner.

The pump may be controlled to pump in both the forward and reverse directions. By pumping in both directions, perfusion solution could be returned to the pump reservoir. Solution could then be returned from the reservoir to the tissue through subsequent pumping in a cyclic manner, for as long as desired.

The perfusion solution preferably contains at least a colloidal agent, an anti-edema agent, an antioxidant, an anti-inflammatory agent and a vasodilator. The perfusion solution may additionally contain one or more additional additives, including oxygenation agents such as perfluorocarbons, pH buffering agents such as HEPES and other additives such as hormones, steroids, penicillin, magnesia and/or insulin.

The colloidal agent serves to effectively remove blood from the afterbirth. Hydroxyethyl starch is a preferred colloidal agent.

The anti-edema agent serves to prevent cell swelling, and should be present in sufficient amount so as to maintain the osmotic pressure of the solution. The osmotic concentration of the perfusion solution ("osmolarity") should preferably be in a range of about 300 to about 400 mOsmols of solute/liter of solution, and most preferably from about 310 to about 350 mOsmols of solute/liter of solution. The perfusion solution should preferably have a pH, temperature corrected to 37° C., within a range of about 7.35 to about 7.45. Suitable anti-edema agents include sugars such as sucrose, dextrose, raffinose, lactobionate, gluconate and mannitol.

The antioxidant should be present in an amount to prevent oxidation of the cells and improve viability of recovered cells, and is preferably glutathione or allopurinol. Other antioxidants which may be added to the perfusion solution include vitamins A, B, C and E, selenium, cysteine, BHT and BHA.

The anti-inflammatory agent is present in an amount effective to prevent substantial inflammation of the umbilical cord and/or placenta. A suitable anti-inflammatory agent is dexamethasone.

The vasodilator should be present in an amount effective to dilate the arteries of the umbilical cord and placenta. Adenosine and nitric oxide are preferred vasodilators.

Suitable perfusion solutions are well known to those of ordinary skill in the art and many are commercially available. Suitable perfusion solutions include the following: BES, BIS-TRIS, BIS-TRIS propane, EPPS, Gly-Gly, HEPES, HEPES sodium salts, MES hydrate, MES sodium salts, MOPS, MOPS sodium salts, PIPES, TAPS, TAPS sodium salts, TAPSO TES, Tricine, Trizma$^R$ base, Trizma$^R$ Hydrochloride, Trizma$^R$ hydrochloride buffer solution, Trizma$^R$ Pre-set crystals, Alsever's Solution, Ames Medium, Basal Medium Eagle, Click's Medium, Dulbecco's Modified Eagle's Medium-high glucose, Dulbecco's Modified Eagle's Medium-low glucose, Dulbecco's Modified Eagle's Medium/Nutrient Mixture F-12 Ham, Dulbecco's Phosphate Buffered Saline, Earle's Balanced Salts, Gey's Balanced Salt Solution, Glasgow Minimum Essential Medium, Grace's Insect Medium, Hanks' Balanced Salt Solution, IPL-41 Insect Medium, Iscove's Modified Dulbecco's Medium, Iscove Modified Dulbecco's Medium, Krebs-Henseleit Buffer Modified, Krebs-Ringer bicarbonate buffer, L-15 Medium (Leibovitz), McCoy's 5A Medium, MCDB 105 Medium, MCDB 110 Medium, MCDB 131 Medium, MCDB 153 Medium, MCDB 201 Medium, Medium 199, Mega Cell™ Dulbecco's Modified Eagle's Medium, Mega Cell™ Dulbecco's Modified Eagles Medium/Nutrient Mixture F-12 Ham, Mega Cell™ Minimum Essential Medium Eagle, Mega Cell™ Minimum Essential Medium/Nutrient Mixture F-12 Ham, Mega Cell™ RPMI-1640 Medium, Minimum Essential Medium Eagle, NCTC 109 medium, Nutrient Mixture F-10 Ham, Nutrient Mixture F-12 Ham, RPMI 1640, RPMI 1640 Medium with L-glutamine and sodium bicarbonate, RPMI 1640 HEPES Modification with 25 mM HEPES without L-glutamine, RPMI-1640 medium Modified with 20 mM Hepes and L-glutamine and sodium bicarbonate, RPMI 1640 Medium with sodium bicarbonate without L-glutamine, RPMI 1640 Medium Dutch Modification with sodium bicarbonate and 20 mM Hepes without L-glutamine, RPMI 1640 medium 10× without glutamine folic acid and sodium bicarbonate, RPMI 1640 medium modified with sodium bicarbonate without methione, cystine and L-glutamine, RPMI 1640 medium modified with sodium bicarbonate without L-glutamine and phenol red, RPMI 1640 medium HEPES modification, with L-glutamine 25 mM HEPES without sodium bicarbonate, RPMI 1640 medium with L-glutamine without glucose and sodium bicarbonate, RPMI 1640 medium modified with L-glutamine without phenol red and sodium bicarbonate, RPMI 1640 medium powder, Auto-Mod™ cell cultured tested, Schneider's insect medium, Shields and Sang M3 insect medium, TC-100 insect medium, TNM-FH insect medium, Tyrode's salts, Waymouth MB 752/1 medium, Williams' medium E, Hanks, Eagles, Albumin, Belzer Machine perfusion solution or generic versions, Celsior or generic versions, Euro-Collins or generic Versions, HTK or generic versions, Lactated Ringers or generic versions, Plasmanate or generic versions, Hespan or generic versions, Normal Saline or generic versions, IGL or generic versions, Vasosol or generic versions, and/or Viaspan or generic versions.

In a preferred embodiment, the perfusion machine pump is primed with a priming solution prior to pulsatile perfusion of the afterbirth tissue. Preferably, the priming solution and the perfusion solution are the same.

The afterbirth tissue is placed into a sterile, closed perfusion circuit, typically by cannulation of the umbilical cord using an appropriate sized, sterile stainless steel or plastic, for example, Teflon® (polytetrafluoroethylene), cannula which is preferably sized from about 2 mm to about 5 mm, and silk ties (01,2,3), or umbilical tape. After being placed in the perfusion circuit, the vasculature is opened to allow the perfusion solution to be discharged from the afterbirth tissue. If exsanguination is desirable for any reason, preferably, the perfusion step is carried out prior to exsanguination. In a preferred method, no exsanguination of the afterbirth tissue is carried out in the performance of the method.

Starting the perfusion pump begins pulsatile perfusion. Preferably, the perfusion pump is operated so as to produce a systolic perfusion pressure in a range of from about 50 to about 150 mmHg, preferably about 90 to about 120 mmHg. The pulsatile perfusion circuit may preferably be operated at a temperature range of from about 4° C. to about 40° C., more preferably, from about 15° C. to about 20° C. Pulsatile perfusion typically avoids undesirable vasospasms of the arterial-vein circuit.

Pulsatile perfusion refers to the rhythmic, intermittent propagation of fluid through a vessel or piping system, in contrast to constant, smooth propagation, which produces laminar flow. The quality of fluid flow, whether smooth (laminar) or pulsatile, is important to the integrity of the tissues being artificially perfused by various devices. Pulsatile perfusion has been demonstrated to offer significant advantages in other areas of clinical significance, including Cardiac and Thoracic surgery. See, for example, "Comparative clinical study of pulsatile and non-pulsatile perfusion in 350 consecutive patients," Hammon J Wi, Extracorporeal Circulation: Perfusion System Cohn Lh, ed. Cardiac Surgery in the Adult. New York: McGraw-Hill, 2008:350-370, "CARDIOPULMONARY BYPASS, MYOCARDIAL MANAGEMENT, AND SUPPORT TECHNIQUES: A RANDOMIZED STUDY OF THE INFLUENCE OF PERFUSION TECHNIQUE AND pH MANAGEMENT STRATEGY IN 316 PATIENTS UNDERGOING CORONARY ARTERY BYPASS SURGERY:II," Neurologic and cognitive outcomes, J. Thorac. Cardiovasc. Surg., 1995; 110:349-362; "The influence of pulsatile and nonpulsatile extracorporeal circulation on fluid retention following coronary artery bypass grafting," Perfusion, Vol. 7, No. 3, 201-211 (1992); and "Pulsatile Perfusion Reduces the Incidence of Delayed Graft Function in Expanded Criteria Donor Kidney Transplantation," American Journal of Transplantation 2006; 6: 1473-1478.

Typical rates for pulsatile perfusion of fluids through tissues or organs, such as afterbirth tissue, would mimic normal physiological rates, for example between 50 and 120 pulses per minute at a rate of 0.5 to 1.5 liters per minute per kilogram of tissue mass.

After perfusion has proceeded to the point that the perfusate runs clear of visible blood products, measurable cellular matter and/or another user-defined end-point, the perfusion solution may be exchanged with digestion solution. Digestion solutions commonly used to disaggregate cell populations from the cytoskeletal framework and connective tissues of the organ or tissues may be employed. The digestion solution may contain standard digestive enzymes well known to those of ordinary skill in the art, such as collagenase or trypsin. Ideally, the temperature is maintained to encourage enzymatic activity and achieve a high viability of recovered cells. The digestion step proceeds as the digestion solution is perfused through the afterbirth tissue until the tissue begins to visually disaggregate or until another user-defined end-point has been achieved.

Following exposure to digestive enzymes, cells are further elutriated by mechanical disruption and subsequent separation from non-digested aggregates and tissues using common methods such as filtration and/or centrifugation. The digested tissue may be removed from the perfusion circuit and mechanically disrupted through methods well known to those of ordinary skill in the art, such as mincing the tissue with scalpels, knife or razor, mincing in a stomacher bag or similar apparatus, straining through cheese cloth, filtration, or blending in a commercial blender. In this manner, additional cells may be extracted from the digested afterbirth through fractionation of the eluate and/or mechanical disruption of the organ.

Cellular matter collected is heavier than the perfusion and/or digestion solution and thus can easily be separated from these solutions. The cells may be isolated from the other blood components using techniques and apparatus well known to those of ordinary skill in the art, such as centrifugation, immuno-magnetic separation, cell sorting and flow cytometry.

EXAMPLE 1

Isolation of Cells

The cells may be isolated by centrifugation using a standard laboratory centrifuge where the material is placed into the centrifuge and centrifuged for 10 minutes at 1,000 rpm to separate out the desired cells from the other extracted components. The cells are then aseptically separated with sterile pipettes and placed into sterile conical tubes with normal saline and or Lactated Ringers solution and centrifuged again for 10 minutes at 1,000 rpm to wash the cells. The cells are again aseptically separated from the wash solution with sterile pipettes and then placed into another set of conical tubes with Ficol Solution and placed in the centrifuge at 1,200 rpm for 5 minutes. The cells may then be aseptically separated from the Ficol Solution with sterile pipettes and placed into sterile tubes for the appropriate storage method. When this process has been completed, a sample of the cells (1 micro liter) will be placed in a flow cytometer to quantify the total number of stem cells that was recovered, and to determine stem cell purity and viability. The cells may then be transferred into appropriate sized containers for distribution and may either be stored at about 4° C. in a refrigerator for immediate use or cryopreserved at about −180° C. and stored in vapor phase liquid nitrogen. Each storage vial or container may preferably be bar coded for identification before storage.

EXAMPLE 2

Isolation of Cells Using a Cell Saver

Another example of a suitable centrifugation method involves placement of the obtained cells into a cardiotomy on a Hemanetics Cell Saver machine. Once all of the obtained cells have been placed into the cardiotomy, the cells will be drained into a centrifuge bowl or basin. After draining, the cell saver may be started in the spin or separation mode. Usually approximately 5 minutes is required to complete this section. The Cell Saver will automatically switch to wash after the separation mode and wash the cells with either a 500 ml bag of Normal Saline or Lactated Ringers solution. The Cell Saver will then separate the wash from the cells and switch to a second wash with Ficol Solution. The Cell Saver may then wash the cells with the Ficol Solution after which the Cell Saver may automatically switch to a centrifuge mode and separate the cells from the Ficol Solution. The Cell Saver may then transfer the cells into a sterile storage bag. When this process has been completed a sample of the cells (1 micro liter) will be placed in a flow cytometer to quantify the total number of cells recovered, and to determine cell purity (by cell type) and viability. The cells may then be transferred into appropriate sized containers for distribution and may either be stored at about 4° C. in a refrigerator for immediate use or cryopreserved at about −180° C. and stored in vapor phase liquid nitrogen. Each storage vial or container may preferably be labeled for identification before storage.

EXAMPLE 3

Isolation of Cells Using a COBE® 2991 Blood Cell Processor

Another suitable centrifugation method may employ the COBE® 2991 Blood Cell Processor (Gambro BCT, Inc.) to separate the cells and white blood cells from red blood cells, plasma and platelets, and then wash, for example with Normal Saline or Lactated Ringer's solution (or Ficols solution).

As discussed above, a centrifugation process may be used to remove the original perfusate solution from the nucleated cells. Typically, this process also removes plasma, platelets and red cells leaving stem cells and white blood cells. However, if it would be preferred to have any of the plasma, platelets and red cell blood components in the product, the centrifugation process can be modified to alter the cells that are removed. For example, the wash cycle of the COBE® 2991 cell sorter system can be adjusted.

A preferred time period for the centrifugation process is to spin the collected perfusate for a time range of about 7 to about 20 minutes at a centrifuge speed of about 500 to about 3,000 revolutions per minute (RPM) to separate the perfusion solution, platelets, plasma, and red cells. A more preferred time setting will be about 10 to about 12 minutes at a centrifuge speed of about 1,000 to about 1,200 RPM. After the first centrifugation step, Ficol Solution can be added as a preservative system to preserve the stem cells before starting the cryopreservation process. From about 250 ml to about 500 ml of Ficol Solution may preferably be added to the remaining cells by gravity and then the centrifugation system may be set to run at a speed of about 2,000 to about 5,000 RPM, more preferably at about 2,500 to about 3,500 RPM, for a time of about 15 to about 30 minutes, more preferably, about 20 minutes. When this process has ended a sample of the cells (1 micro liter) may be placed in a flow cytometer to quantify the total number of cells that was recovered, and to determine cell purity (by cell type) and viability. The cells may then be transferred into appropriate sized containers for distribution and may either be stored at about 4° C. in a refrigerator for immediate use or cryopreserved at about −180° C. and stored in vapor phase liquid nitrogen. Each storage vial or container may preferably be labeled for identification before storage.

Whether the isolated cells are used immediately or cryopreserved for later use, a sample of the placental blood may be used to identify the human lymphocyte antigens (HLA) of the cell populations and the blood serotype of the cells.

The cells obtained by the method of the present invention may be used to create a cell line by placing them in a tissue culture medium, which contains appropriate nutrients, and permitting the cells to grow. Suitable culturing conditions for CD34+ cell populations include agar media for the cells to grow different types of colonies (General, Erythroid colonies, Granulopoietic colonies, Multi-linage colonies, Megakaryocyte colonies, Blast colonies, Polycythemia Vera Colonies (PV), Chronic Myeloid Leukemia Colonies (CML), Myelodysplastic Syndromes (MDS) and Acute Myeloid Leukemia (AML) Colonies. In order to grow colonies the appropriate culture media will be used and then the cells will be placed into a $CO_2$ incubator at an established temperature and humidity. Set forth below are two illustrative $CO_2$ tissue culture media:

| Methycellulose Medium containing Agar LCM* | |
|---|---|
| 0.9% | Methycellulose |
| 30% | Fetal Bovine Serum |
| 1% | Bovine Serum Albumin |
| $10^{-4}$ M | 2-Mercaptoethanol |
| 10% | Agar LCM |
| 3 units/ml | Erythropoietin |
| 60% | Iscove's DMEN |

| Methylcellulose Medium Containing RC* | |
|---|---|
| 0.9% | Methylcellulose |
| 30% | Fetal Bovine Serum |
| 1% | Bovine Serum Albumin |
| $10^{-4}$ M | 2-Mercaptoethanol |
| 2 mM | L-Glutamine |
| 50 ng/ml | Stem Cell Factor |
| 10 ng/ml | Gm-CSF |
| 10 ng/ml | IL-3 |

-continued

| Methylcellulose Medium Containing RC* | |
|---|---|
| 3 units/ml | Erythropoetin |
| 70% | Iscove's DMEN |

*Formulas taken from "Atlas of Human Hematopoietic Colonies" Published by Stem cell Technologies, Inc.

Suitable culturing conditions for other cell populations are widely published in scientific literature and include any number of standard cell culture medium supplemented with serum, cytokines growth factors and other essential amino acids and proteins.

The present invention provides a method for the non-controversial production of non-embryonic, pluripotent stem cells in significant amounts as well as desirable primary cell types such as endothelium, epithelium, keratinocytes, neurons, myocytes, lymphocytes, leukocytes, and eosinaphils. More particularly, the method is believed capable of removing 90% or greater of the stem cell colonies from afterbirth tissue, with 90% or greater purity. These cells may be used as is, or may be cultured and grown into cell lines.

Applications for products produced by the process of the present invention include pediatric and adult non-related bone marrow recipients, trauma patient recovery care; reconstructive surgeries such as removing wrinkles, breast enlargements and reductions, and other reconstructive surgeries where minimum scarring is permissible, vaccine development, drug development, and research generally, including research directed to curing Alzheimer's, Parkinson's, and diabetes. These cells may also be used for the regeneration of nerve tissue, and development of new organs.

EXAMPLE 4

Cell Collection Using Pulsatile Perfusion

In this example, the feasibility of using machine pulsatile perfusion to collect human umbilical cord blood (UCB) total nucleated cells and CD34+ HSCs was evaluated using placentas designated for research purposes. UCB (65+15 mL, n=5) was first collected by needle aspiration from the umbilical cord vein in accordance with standard procedures then followed by machine pulsatile perfusion (MPP) (~500 ml) of the placental arteries within 2-3 hours of delivery Clinically, total nucleated cells count (TNC), CD34+ cell numbers and myeloid, erythroid and multipotent CFU progenitor cell content of UCB units, are used as predictive measurements of hematopoieticlengraftment potential. Low-density cells (<1.077 g/mL) were isolated by density centrifugation. The median number of viable low density cells obtained was $488 \times 10^6$ (range, $240\text{-}652 \times 10^6$), and $1541 \times 10^6$ (range, $888\text{-}1800 \times 10^6$) for UCB and MPP collections, respectively.

MPP low density cell preparations contained significantly more mature segmented neutrophils with a low percentage (<0.1%) of sheared-off vessel wall endothelial cells present, Both UCB and MPP low density cell collections showed similar number of CFU-GEMM, CFU-GM, CFU-M, and CFU-G progenitor cells. MPP collected cells contained 2-3 times more assayable erythroid BFU-E colonies than UCB collections. Equal numbers of CD34+ HSC enumerated by FACS analysis and isolated by positive immunomagnetic selection from MPP and UCB collections. Likewise, the number of assayable CFU-GEMM, CFU-GM, CFU-M, CFU-G and BFU-e progenitor cells from isolated CD34+ cells derived from each cell collection were very similar.

These results demonstrate that pulsatile perfusion can be performed to effectively recover on average twice as many TNC and multilineage CD34+ HSC cells when compared to traditional UCB collection procedures. Altogether these results are particularly promising since increased numbers of UCB HSC available for infusion should result in accelerated hematopoietic recovery. The simplicity, speed of collection and then number of total HSC collected could clinically widen the applicability of UCB transplants in adults.

The invention claimed is:

1. A method for extracting nucleated cells from afterbirth tissue, comprising the steps of:
   a) locating the afterbirth tissue in a perfusion circuit without exsanguination of said afterbirth tissue;
   b) extracting nucleated cells from said non-exsanguinated afterbirth tissue by pulsatile perfusion carried out using a rhythmic, intermittent flow of a perfusion solution pulsed at between 50 and 60 pulses per minute to produce a perfusate containing cells; and
   c) isolating said nucleated cells from the perfusate.

2. The method of claim 1, further comprising the step of administering an anticoagulant to said afterbirth tissue prior to locating said afterbirth tissue in said perfusion circuit.

3. The method of claim 1, wherein said perfusion solution comprises a colloidal agent, an anti-edema agent, an antioxidant, an anti-inflammatory agent and a vasodilator.

4. The method of claim 1, wherein said perfusion solution is selected from the group consisting of BES, BIS-TRIS, BIS-TRIS propane, EPPS, Gly-Gly, HEPES, HEPES sodium salts, MES hydrate, MES sodium salts, MOPS, MOPS sodium salts, PIPES, TAPS, TAPS sodium salts, TAPSO TES, Tricine, TRIS base, TRIS hydrochloride, TRIS hydrochloride solution, TRIS crystals, Alsever's Solution, Ames Medium, Basal Medium Eagle, Click's Medium, Dulbecco's Modified Eagle's Medium-high glucose, Dulbecco's Modified Eagle's Medium-low glucose, Dulbecco's Modified Eagle's Medium/Nutrient Mixture F-12 Ham, Dulbecco's Phosphate Buffered Saline, Earle's Balanced Salts, Gey's Balanced Salt Solution, Glasgow Minimum Essential Medium, Grace's Insect Medium, Hanks' Balanced Salt Solution, IPL-41 Insect Medium, Iscove's Modified Dulbecco's Medium, Iscove Modified Dulbecco's Medium, Krebs-Henseleit Buffer Modified, Krebs-Ringer bicarbonate buffer, L-15 Medium (Leibovitz), McCoy's 5A Medium, MCDB 105 Medium, MCDB 110 Medium, MCDB 131 Medium, MCDB 153 Medium, MCDB 201 Medium, Medium 199, Dulbecco's Modified Eagle's Medium, Dulbecco's Modified Eagles Medium/Nutrient Mixture F-12 Ham, Minimum Essential Medium/Nutrient Mixture F-12 Ham, RPMI-1640 Medium, Minimum Essential Medium Eagle, NCTC 109 Medium, Nutrient Mixture F-10 Ham, Nutrient Mixture F-12 Ham, RPMI 1640, RPMI 1640 Medium with L-glutamine and sodium bicarbonate, RPMI 1640 HEPES Modification with 25 mM HEPES without L-glutamine, RPMI-1640 medium Modified with 20 mM Hepes and L-glutamine and sodium bicarbonate, RPMI 1640 Medium with sodium bicarbonate without L-glutamine, RPMI 1640 Medium Dutch Modification with sodium bicarbonate and 20 mM Hepes without L-glutamine, RPMI 1640 medium 10× without glutamine, folic acid and sodium bicarbonate, RPMI 1640 medium modified with sodium bicarbonate without methione, cystine and L-glutamine, RPMI 1640 medium modified with sodium bicarbonate without L-glutamine and phenol red, RPMI 1640 medium HEPES modification, with L-glutamine 25 mM HEPES without sodium bicarbonate, RPMI 1640 medium with L-glutamine without glucose and sodium bicarbonate, RPMI 1640 medium modified with L-glutamine without phenol red and sodium bicarbonate, RPMI 1640 medium powder, Schneider's insect medium, Shields and Sang M3 insect medium, Shields and Sang M3 insect medium, TC-100 insect medium, TNM-FH insect medium, Tyrode's salts, Waymouth MB 752/1 medium, Williams' medium E, Hanks, Eagles, Albumin, Belzer Machine perfusion solution, Celsior, Euro-Collins, HTK, Lactated Ringers, Plasmanate, Hespan, Normal Saline, IGL, Vasosol, and Viaspan.

5. The method of claim 1, wherein said perfusion solution has a pH, temperature, corrected to 37° C., within a range of about 7.35 to about 7.45, and an osmolality in a range of about 300 to about 400 mOsmols.

6. The method of claim 5, wherein said osmolality is in the range from about 310 to about 350 mOsmols.

7. The method of claim 1, wherein said perfusion solution is perfused through said afterbirth tissue at a systolic perfusion pressure from about 50 to about 150 mmHg, and at a temperature from about 4° C. to about 40° C.

8. The method of claim 7, wherein said systolic perfusion pressure is in the range from about 90 to about 120 mmHg, and the temperature is in the range from about 15° C. to about 20° C.

9. The method of claim 1, further comprising the step of priming a pump of a perfusion machine used in the method with a priming solution prior to said extracting step.

10. The method of claim 9, wherein said priming solution has the same composition as said perfusion solution.

11. The method of claim 1, wherein said nucleated cells are isolated from said perfusate using at least one method selected from the group consisting of centrifugation, immunomagnetic separation, cell sorting and flow cytometry.

12. The method of claim 1, wherein said pulsatile perfusion simulates a pulsed flow of a beating heart.

13. The method of claim 1, further comprising the step of adding at least one digestive enzyme to the perfusion circuit to produce digested afterbirth tissue.

14. The method of claim 13, wherein said at least one digestive enzyme is added to the perfusion circuit upon completion of said extracting step.

15. The method of claim 14, further comprising the step of extracting the nucleated cells from the digested afterbirth tissue through fractionation of the eluate and/or mechanical disruption of the organ.

16. The method of claim 15, wherein the digestive enzyme is capable of disaggregating cell populations from the cytoskeletal framework and connective tissues of the organ or tissues.

17. The method of claim 15, wherein the digestive enzyme is selected from the group consisting of collagenase and trypsin.

18. The method of claim 1, further comprising the step of culturing the nucleated cells isolated from the perfusate to obtain a cell line from said nucleated cells.

19. A method for extracting nucleated cells from afterbirth tissue, comprising the steps of:
  a) locating the afterbirth tissue in a perfusion circuit without exsanguination of said afterbirth tissue;
  b) extracting nucleated cells from said non-exsanguinated afterbirth tissue by pulsatile perfusion that simulates a pulsed flow of a beating heart at a rate of 50-60 pulses per minute using a perfusion solution to produce a perfusate containing cells; and
  c) isolating the nucleated cells from the perfusate.

* * * * *

UNITED STATES PATENT AND TRADEMARK OFFICE
CERTIFICATE OF CORRECTION

PATENT NO.        : 8,673,547 B2                                                     Page 1 of 1
APPLICATION NO.   : 12/530236
DATED             : March 18, 2014
INVENTOR(S)       : Frederick A. Gage It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 668 days.

Signed and Sealed this
Twenty-ninth Day of September, 2015

Michelle K. Lee
*Director of the United States Patent and Trademark Office*